United States Patent [19]
Tower

[11] Patent Number: 5,868,783
[45] Date of Patent: Feb. 9, 1999

[54] INTRAVASCULAR STENT WITH LIMITED AXIAL SHRINKAGE

[75] Inventor: Allen J. Tower, North Lawrence, N.Y.

[73] Assignee: Numed, Inc., Nicholville, N.Y.

[21] Appl. No.: 834,414

[22] Filed: Apr. 16, 1997

[51] Int. Cl.⁶ .................................................. A61M 29/00
[52] U.S. Cl. ............................... 606/198; 606/194; 623/1; 623/12
[58] Field of Search ..................... 606/198, 194, 606/195, 191, 108; 623/1, 12

[56] References Cited

U.S. PATENT DOCUMENTS

| | | |
|---|---|---|
| 4,718,907 | 1/1988 | Karwoski et al. ........................... 623/1 |
| 4,733,665 | 3/1988 | Palmaz . | 
| 5,161,547 | 11/1992 | Tower . |
| 5,217,483 | 6/1993 | Tower . |
| 5,383,892 | 1/1995 | Cardon et al. ........................... 606/198 |
| 5,613,981 | 3/1997 | Boyle et al. . |
| 5,643,279 | 7/1997 | Trotta ....................................... 606/194 |

*Primary Examiner*—Michael Buiz
*Assistant Examiner*—Kevin Truong
*Attorney, Agent, or Firm*—Wall Marjama Bilinski & Burr

[57] ABSTRACT

A radially expandable stent for implantation in a body blood vessel includes a pair of cylindrically shaped end portions made from a malleable metal and formed in a radially expandable fashion. According to the invention, the end portions are joined by a plurality of individual longitudinal wire members such that upon radial expansion of the stent, such as through use of a balloon catheter, the stent expands radially with a minimum of lateral shrinkage. Preferably, the longitudinal wire members are wrapped to the end portions to form flexible hinging sites upon expansion.

7 Claims, 4 Drawing Sheets

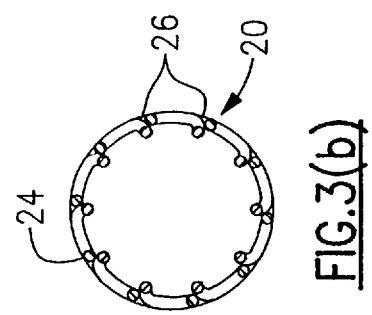
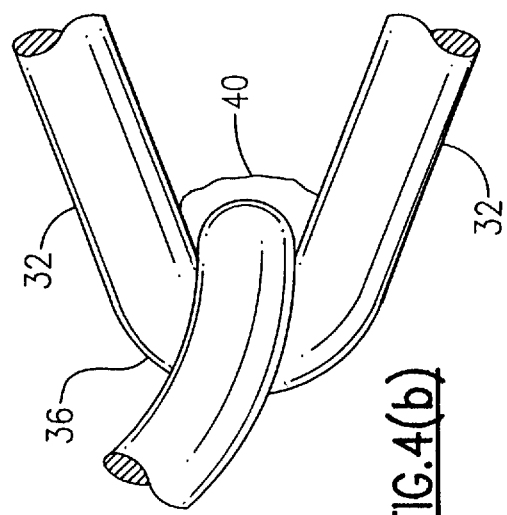
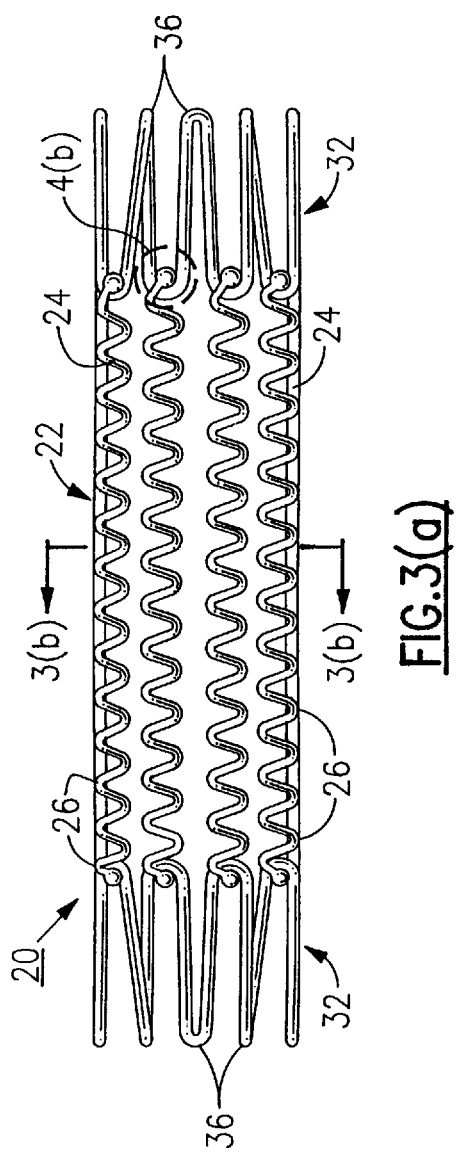
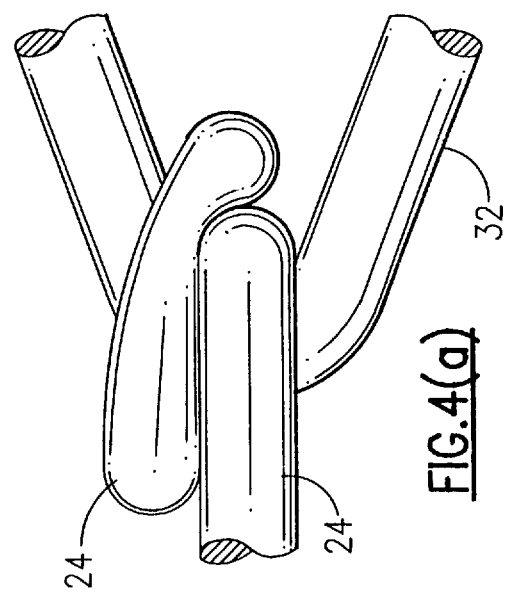

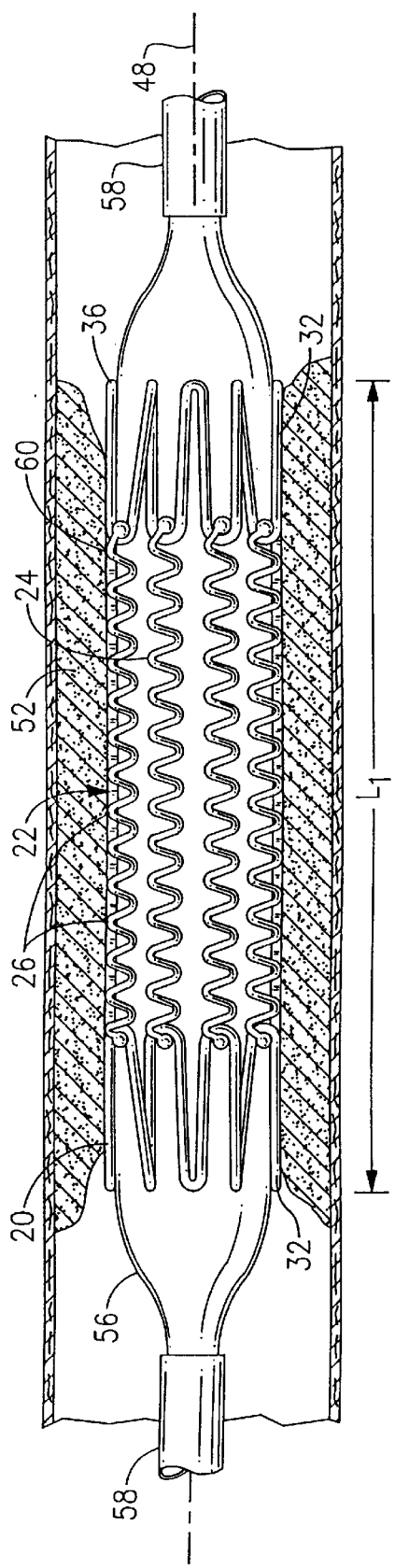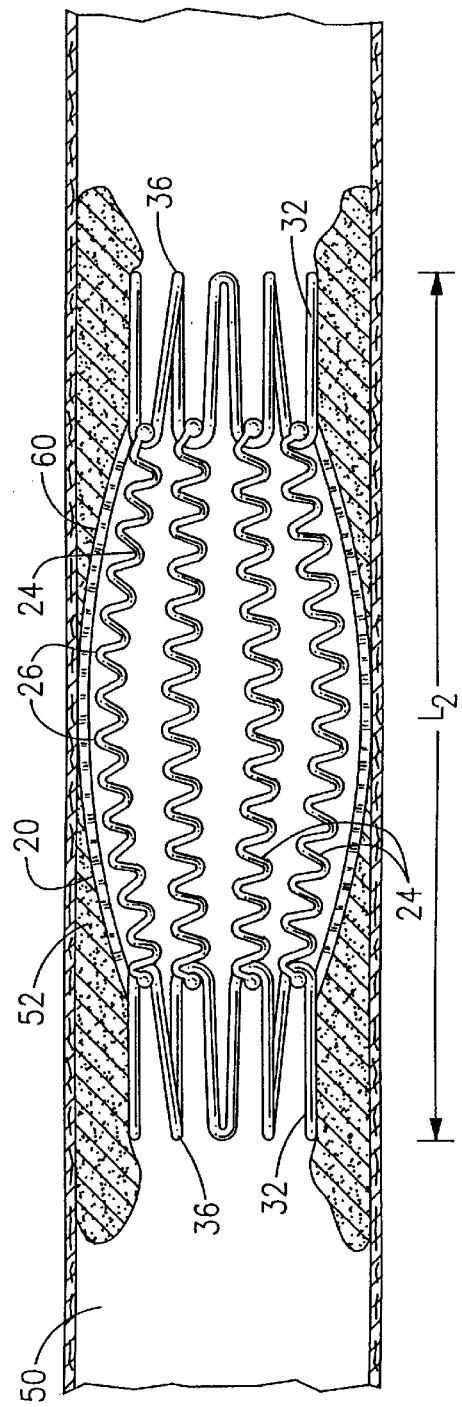

5,868,783

INTRAVASCULAR STENT WITH LIMITED AXIAL SHRINKAGE

FIELD OF THE INVENTION

The invention relates to the field of implantable intravascular stents, and more particularly to an implantable intravascular stent which can be radially expanded, such as by balloon catheterization, with only limited radial shrinkage.

BACKGROUND OF THE INVENTION

Known radially expandable intravascular stents include a cylindrically shaped sleeve having a first diameter which is placed over a collapsed balloon catheter and then inserted into an occluded or partially occluded blood vessel of interest. Upon inflation of the balloon to a specific pressure, the stent is permanently deformed to a larger second diameter and into contact and support with the interior walls of the blood vessel. After subsequent deflation of the balloon and removal of the catheter, the implanted stent remains supported to the interior wall of the blood vessel at the expanded second diameter.

Intravascular stents such as described in U.S. Pat. No. 4,733,665, issued to Palmaz, included a number of interconnected elongate elements, made from a material such as stainless steel or tantalum, which are arranged and welded in a criss-cross arrangement to form a unitary cylindrical structure. An implanted stent of this construction is shown in FIG. 1 as positioned in an occluded blood vessel of interest. After inflation of the collapsed catheter balloon, however, the overall radial expansion of the instant stent creates a corresponding lateral or axial shrinkage, as shown in FIG. 2, whereby the net result may be a less than successful implantation procedure.

Stents, such as those described by Palmaz, are designed to be expanded only a single time and only to a specific diameter. Therefore, even properly implanted stents of this type may not produce a satisfactory result, particularly in procedures involving children, having blood vessels which will naturally increase in size over time. That is, additional axial shrinkage will occur upon reexpanding of the implanted stent to compensate for the growing blood vessel.

It would be preferred to be able to implant an intravascular stent capable of further radial expansion to at least one greater radial diameter, at a later time as needed. More preferably, it would be preferable to provide a stent capable of radial expansion with a minimum of axial shrinkage.

SUMMARY OF THE INVENTION

It is a primary object of the present invention to improve the design of radially expandable intervascular stents.

It is a further object of the present invention to provide an implantable intravascular stent which has limited axial shrinkage, even upon radial expansion of the stent after implantation.

It is a further object of the present invention to provide an intravascular stent capable of expanding over a range of radial diameters while exhibiting minimal overall axial shrinkage over that range.

Therefore, and according to a preferred aspect of the present invention, there is provided a radially expandable stent for intravascular implantation, said stent comprising:
a pair of end portions, said end portions being fabricated of a continuous malleable metal wire having a first set of sinusoidal bends would into a cylindrical sleeve;
a plurality of longitudinally extending sections, each said section being fabricated of a continuous malleable metal wire, and having a second set of sinusoidal bends extending along its length; and
means for separately attaching individual ends of said longitudinally extending sections to each of said end portions to define a cylindrical form having a first radial diameter, wherein said longitudinally extending sections and said end sections are capable of radially expanding to at least a second radial diameter in conformance with the profile of an expanded catheter balloon onto which said stent is positioned for implantation within a blood vessel, in which said first set of sinusoidal bends are circumferentially disposed and said second set of sinusoidal bends are laterally disposed such that inflation of said balloon expands said stent from said first radial diameter to said at least said second radial diameter with minimal axial shrinkage.

Preferably, the ends of each of the longitudinally extending wire portions are separately wrapped to each of the circumferential end portions to provide flexible hinging points or sites.

According to another aspect of the present invention, there is provided a method of forming a radially expandable stent for intravascular implantation, comprising the steps of:
separately forming a first set of sinusoidal bends in at least two malleable metal wires;
individually bending each of said malleable metal wires into a cylindrical form, said form defining end portions of said stent;
forming a second set of sinusoidal bends in a plurality of longitudinal members, said members being made from a malleable metal wire;
attaching one set of ends of said plurality of longitudinal wire members individually to an end portion by attaching each said end to one of said first set of circumferential sinusoidal bends of said end portion; and
attaching the remaining ends of said plurality of longitudinal wire members individually to said other of said at least two end portions by attaching each said end to said first set of sinusoidal bends, wherein said first set of sinusoidal bends extends circumferentially and said second set of sinusoidal bends extends laterally relative to a center axis.

According to yet another preferred aspect of the present invention, there is disclosed a stent implantation system comprising;
a balloon catheter having a collapsible catheter balloon; and
a radially expandable stent including a cylindrical sleeve having a first radial diameter for conforming to said collapsible catheter balloon, said stent further including a middle portion comprising a plurality of longitudinally extending wire portions having a first set of sinusoidal bends extending laterally relative to a center axis, said wire portions further including respective ends interconnected to a pair of circumferential end portions formed of a malleable metal wire having a second set of sinusoidal bends formed into a cylindrical sleeve, wherein said second set of sinusoidal bends extend circumferentially relative to said center axis, allowing said stent to expand from said first radial diameter to at least one larger second radial diameter with minimal axial shrinkage of said stent.

An advantage of the present invention is that an intravascular stent is provided which can be radially expanded, such as by a balloon catheter, to an increased radial dimension with a minimum of axial shrinkage, found in prior art stents used for the same purposes.

Another advantage of the present invention is that the described stent is particularly useful for children because the stent can be subsequently expanded over a range of radial diameters to account for the growth of the blood vessel into which the stent is implanted.

Other objects, features, and advantages will be apparent from the following Detailed Description of the Invention when read with the accompanying drawings.

BRIEF DESCRIPTION OF THE DRAWINGS

FIG. 3(a) is an side elevational view of a radially expandable stent in accordance with a first embodiment of the present invention;

FIG. 3(b) is an end view of the stent of FIG. 3(a);

FIG. 4(a) is an enlarged view of a portion of the circumferential and lateral wire portions of the stent of FIGS. 3(a) and 3(b), showing an interconnection therebetween;

FIG. 4(b) is the enlarged view of FIG. 4(a), showing an alternate interconnection between the circumferential and lateral wire portions of the stent;

FIG. 5 is a side elevational view, partially in section, of the stent of FIGS. 3(a) and 3(b) as implanted in a blood vessel by an uninflated balloon catheter;

FIG. 6 is the side elevational view of the stent of FIG. 5 after inflation and removal of the catheter.

DETAILED DESCRIPTION OF THE INVENTION

Figure 1:
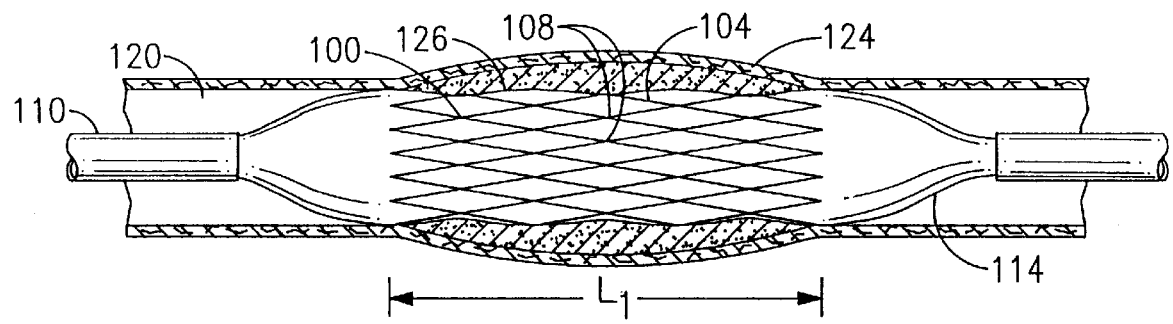
FIG. 1 is a side elevational view, partially in section, of a balloon catheter implantation of a radially expandable intravascular stent according to the prior art.
Figure 2:
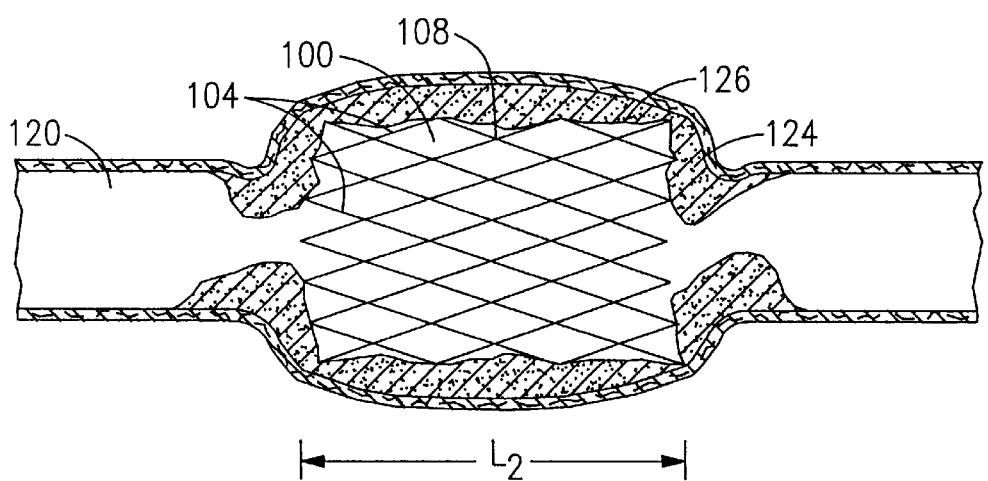
FIG. 2 is the side elevational view of the stent of FIG. 1 upon inflation and removal of the balloon catheter.

As referred to in the preceding, FIGS. 1 and 2 illustrate a radially expandable prior art stent 100, such as described by U.S. Pat. No. 4,733,665, issued to Palmaz, which is placed over a collapsed balloon catheter 110 and positioned within a blood vessel 120 of interest having an occluded portion 124. The collapsed catheter balloon 114 is then inflated to allow the stent 100 to controllably assume a second radial diameter, shown in FIG. 2, in contact with the interior wall 126 of the blood vessel 120. The stent 100 is formed of a series of interconnected criss-crossing elongate members 104 which are welded at intersecting points 108 to define a unitary cylindrical structure which expands uniformly upon inflation. As is apparent, an increase in radial size of the stent causes a corresponding decrease in length, shown figuratively as the difference between $L_1$ and $L_2$, whereby the described stent 100 could lose as much as 40–50 percent or more in length due to the axial shrinkage.

Referring now to FIGS. 3(a) and 3(b), there is shown a radially expandable intravascular stent in accordance with a preferred embodiment of the present invention. The stent 20 includes a center portion 22 defined by a plurality of individual longitudinally extending wire members 24, each member being fabricated from a soft malleable metal. According to this embodiment, the wire members are fabricated from a fine platinum wire having a diameter of approximately 0.007", which is annealed prior to forming to remove as much spring memory as possible. The wire before bending, being in the fully annealed condition, will retain whatever shape it is firmed into. Each of the longitudinally extending wire members 24 are provided with a series of sinusoidal bends 26 having a frequency of approximately 10 cycles per inch and an amplitude (width) of approximately 1/16". The wire members 24 described in this specific embodiment include 8 sinusoidal bends 26, which are formed in any convenient manner, for instance by bending about a rack gear (not shown) by running a corresponding spur gear (not shown) over a wire lad over the rack. This method is further described in commonly assigned U.S. Pat. No. 5,161,547, issued to Tower, the contents of which are herein incorporated in their entirety. It is contemplated that wires having a range of suitable diameters e.g., between 0.002 and 0.15 inches, can alternately be used. Alternate materials are described in commonly assigned and co-pending U.S. patent application No. 60/027,345, filed Oct. 10, 1996, which is herebey incorporated by reference in its entirety.

A pair of circumferential end portions 32, preferably fabricated from the same malleable metal wire material, are also formed with a series of sinusoidal bends 36. According to this embodiment, the sinusoidal bends 36 have a frequency of approximately 50 cycles per inch and are formed preferably in like manner as those provided on the longitudinally extending members 24. The sinusoidal bends 36 of the end portions 32 are suitably longer than those previously formed in the longitudinally extending wire members 24, having an amplitude of approximately 5/16", to allow the stent 20 to radially expand over a larger radial range as described in greater detail below. The end portions 32 according to this embodiment include 10 bends 36 over its length.

After the sinusoidal bends 36 have been formed, the end portions 32 are wound onto a mandrel (not shown) to form a cylindrical sleeve of suitable diameter, about 0.60" (approximately 1.5 mm) according to this embodiment. The respective ends (not shown) of the formed sleeve are then attached at either end of the wrap, preferably by welding or other securing means.

The fabrication of the stent 20 is completed by attaching each of the respective ends 40 of the longitudinally extending wire sections 24 as shown in FIG. 4(a) to each of the sinusoidal bends 36 of the circumferential end portions 32 by wrapping each wire end 40 around a corresponding loop 44. Preferably, the wire ends 40 are wrapped one and one half revolutions. As described below, this form of attachment provides a flexible hinge between the wire members 24 and the end portions 32. Alternately, the ends 40 can be laser-welded or other known fusing techniques, as shown in FIG. 4(b).

Preferably, and as shown in the sectional end view of FIG. 3(b), the upper into an appropriate human blood vessel 50 having an occluded region 52. Initially, the stent 20 is placed in overlaying relationship to a collapsed balloon catheter 58 The stent 20 has a diameter of approximately 1.5 mm (0.060") for insertion into the blood vessels adjacent the heart.

The catheter balloon 56 is preferably made from a nylon or other flexibly expandable material and the stent 20 is crimped thereon in a manner such as described in copending and commonly assigned U.S. Ser. No. 08/834,430, [Attorney Docket 212_027], or by other means which insures the stent is placed on the catheter with sufficient adherence to prevent shifting during positioning in the blood vessel 50. The catheter 58 is then guided into the desired location within the blood vessel 50 by means of an introducer (not shown) using a guide wire (not shown) in a manner known to those of skill in the art.

The stent 20, being made of a malleable metal, can assume a crimped position on the collapsed catheter balloon 56 without sacrificing its intended function and with minimal risk of puncturing the balloon. Once the stent is properly located and verified by fluoroscopic or other means, the collapsed catheter balloon 56 is then inflated in a manner commonly known and the stent 20 is radially expanded in conformity with the expansion of the balloon profile due to the malleability of the stent material. According to this embodiment, a pressure of about 100 psi is sufficient to inflate the stent 20 to a diameter of approximately 8 mm, and into contact with the interior wall 60 of the occluded region 52, though it will be understood to those of skill in the field that other suitable pressure can be contemplated. With the present stent, radial expansion of 20 mm or higher without shrinkage has been found to be entirely satisfactory.

As is shown in FIG. 6, the radial expansion of the stent 20 causes the elastic limit of the platinum wire material to be exceeded such that each of the sinusoidal bends 26 of the longitudinal wire members 24 will open as pushed outwardly by the force of the expanding balloon 56. In like manner, the expansion of the balloon also causes the sinusoidal bends 36 of the circumferential end portions 32 to similarly open. Because the ends 40 of the longitudinal wire members 24 are hinged to the cylindrical sleeve assumed by the circumferential end portions 32, there is little tendency for the middle portion 22 of the stent 20 to axially shrink. The only axial shrinkage is exhibited by the circumferential end portions 32 which shrink minimally as the bends 36 are opened. In the described stent, a radial expansion to approximately 8 mm produces an axial shrinkage of approximately 1 mm, or less than 10 percent of the length of the stent 20.

Furthermore, the described stent can be subsequently expanded by reinserting the collapsed balloon catheter into the blood vessel and into alignment with the stent. Because the stent is made of a radiopaque material, its position can be easily tracked. reinflation of the collapsed catheter balloon 56 to an increased diameter will allow the stent 20 to additionally expand for reengagement with the interior wall of the blood vessel. This procedure can be repeated as necessary with the stent preferably being able to expand over a range which includes, for example, an adult sized vessel.

Figure 7:
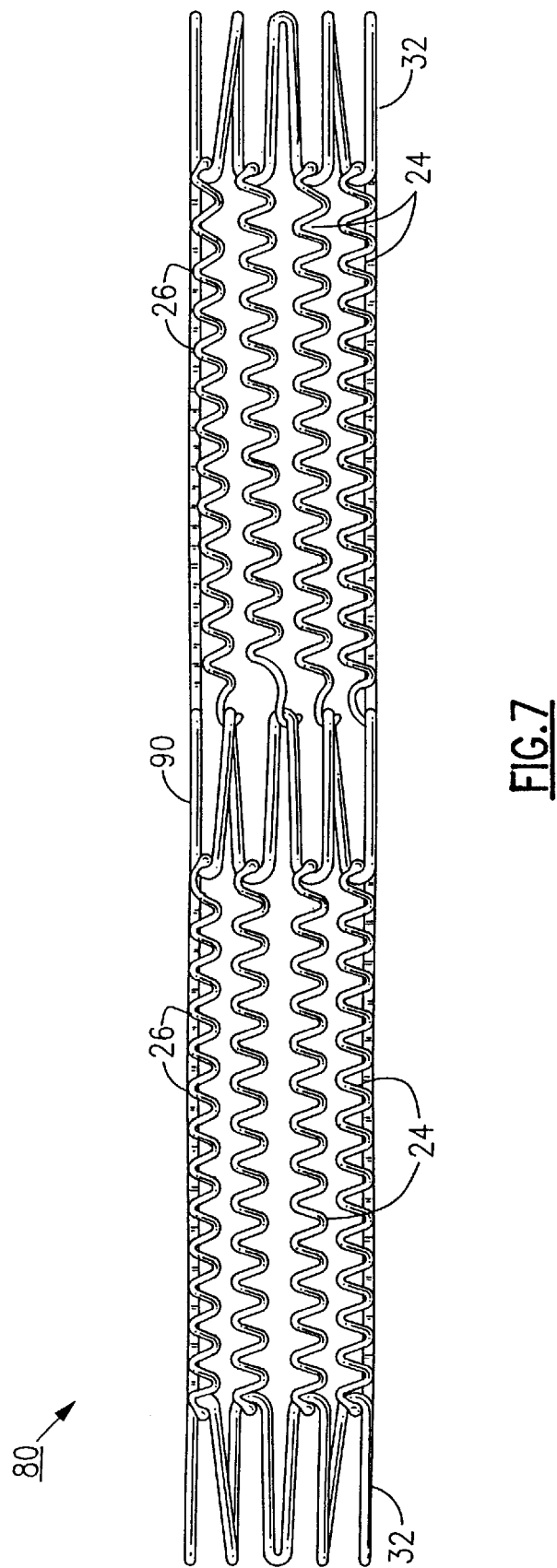
FIG. 7 is a side elevational view of a stent in accordance with a second embodiment of the present invention.

An alternate configuration of a stent 80 according to the present invention is illustrated in FIG. 7. According to this embodiment, an additional circumferential portion 90 is positioned in the middle of the length of the stent between separate pluralities of the longitudinally extending wire sections 24. The circumferential section 90 is fabricated in the same manner as those circumferential end portions 32 on either end and includes sinusoidal bends 36 as described above with the individual ends 40 of the wire members being similarly attached thereto. Providing at least one middle circumferential portion 90 is acceptable for longer implantable stents to similarly minimize axial shrinkage. It will be readily apparent that other stent designs having differing lengths of longitudinal wire sections and/or numbers of intermediately disposed circumferential sections can be easily imagined.

PARTS LISTS FOR FIGS. 1–7

20 stent
22 center portion
24 longitudinal wire members
26 sinusoidal bends
32 circumferential end portions
36 sinusoidal bends
40 ends
44 loops
48 center axis
50 blood vessel
52 occluded region
56 catheter balloon
58 catheter
60 interior wall
80 stent
90 circumferential section
100 stent
104 elongate members
108 intersecting points
110 balloon catheter
114 balloon
120 blood vessel
124 occluded portion
126 interior wall
$L_1$ stent length prior to expansion
$L_2$ stent length after expansion Though the present invention has been described according to specific embodiments, it will be readily apparent that various modifications and changes should be contemplated by those of skill in the field which are within the spirit and scope of the invention, as defined by the appended claims.

I claim:

1. A radially expandable stent for intravascular implantation, said stent comprising:

a pair of end portions, said end portions being fabricated of a continuous malleable metal wire having a first set of sinusoidal bends wound into a cylindrical sleeve;

a plurality of longitudinally extending sections, each said section being fabricated of a continuous malleable metal wire, and having a second set of sinusoidal bends extending along its length; and means for separately attaching individual ends of said longitudinally extending sections to each of said end portions to define a cylindrical form having a first radial diameter, wherein said longitudinally extending sections and said end portions are capable of radially expanding to at lease a second radial diameter in conformance with the profile of an expandable catheter balloon onto which said stent is positioned for implantation within a blood vessel, in which said first set of sinusoidal bends are circumferentially disposed and said second set of sinusoidal bends are laterally disposed such that inflation of said balloon expands said stent from said first radial diameter to said at least said second radial diameter with minimal axial shrinkage.

2. A stent as recited in claim 1, wherein each individual end of said longitudinally extending sections are welded to each of said end portions.

3. A stent as recited in claim 1, wherein the ends of each of said longitudinally extending sections are wrapped around a sinusoidal bend of said circumferential end portions to form a flexible hinging site.

4. A stent as recited in claim 1, wherein said circumferential end portions and said longitudinally extending sections are fabricated from an annealed platinum.

5. A stent as recited in claim 1, wherein each of said sinusoidal bends of said circumferential end portions and said laterally extending sections are bent inwardly toward a center axis of the stent.

6. A stent as recited in claim 1, wherein said stent is capable of being expanded over a range of radial diameters.

7. A stent as recited in claim 1, including at least one additional circumferential portion intermediately disposed between pluralities of longitudinally extending wire members individually attached thereto, said circumferential portion having a series of circumferentially disposed sinusoidal bends.

\* \* \* \* \*